US00PP27329P3

(12) United States Plant Patent
Robacker et al.

(10) Patent No.: US PP27,329 P3
(45) Date of Patent: Nov. 1, 2016

(54) ***VITEX AGNUS-CASTUS* PLANT NAMED 'V0509A-7'**

(50) Latin Name: *Vitex agnus-castus*
Varietal Denomination: V0509A-7

(71) Applicant: University of Georgia Research Foundation, Inc., Athens, GA (US)

(72) Inventors: Carol D. Robacker, Peachtree City, GA (US); Amanda J. Hershberger, San Jose, CA (US); David A. Knauft, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 96 days.

(21) Appl. No.: 14/121,998

(22) Filed: Nov. 12, 2014

(65) Prior Publication Data

US 2016/0135348 P1 May 12, 2016

(51) Int. Cl.
*A01H 5/02* (2006.01)

(52) U.S. Cl.
USPC ..... Plt./226

(58) Field of Classification Search
USPC ..... Plt./226, 216
See application file for complete search history.

*Primary Examiner* — June Hwu
(74) *Attorney, Agent, or Firm* — Klarquist Sparkman, LLP

(57) ABSTRACT

A *Vitex agnus-castus* plant named 'V0509A-7' has upright, large panicles, with white flowers borne more closely along the rachis, resulting in a stunning floral display.

2 Drawing Sheets

Genus and species: *Vitex agnus-castus.*

Varietal denomination: The new *Vitex agnus-castus* claimed is of the cultivar denominated 'V0509A-7'.

BACKGROUND OF THE INVENTION

The present invention relates to a new and distinct cultivar of *Vitex agnus-castus* hereinafter referred to as 'V0509A-7'.

Pedigree and history: 'V0509A-7' originated from a cross of *Vitex agnus-castus* 'Abbeville Blue' (unpatented, female parent) and *Vitex agnus-castus* 'Silver Spires' (unpatented, male parent), caged together with honeybees as pollinators, in the summer of 2005, under the direction of David Knauft. Seeds were collected from 'Abbeville Blue', and may have resulted from self-pollination or crosses with 'Silver Spires'. These seeds were sown, and the seedlings were grown in the spring and summer of 2006. Sixteen plants were selected based on desirable horticultural qualities, and were propagated via stem cuttings in August 2006. In April 2007, the resulting liners were transplanted into containers or the field at a location in Watkinsville, Ga. Based on container and field performance, the plant identified by the cultivar name 'V0509A-7' was selected. Stem cuttings were made from this selected plant, and distributed to Carol Robacker, who took over this breeding program in 2009. Asexually propagated 'V0509A-7' plants, propagated in Griffin, Ga. by stem cuttings in 2009, were planted in a replicated field plot (three reps, randomized block design) in Griffin, Ga. (cold hardiness zone 8a) in fall, 2009.

Plants have been evaluated for four years at the Griffin, Ga. site. Height and width data has been collected annually. Cold damage was assessed each spring. Mean panicle length and number of panicles per compound panicle were counted each summer. First bloom and re-bloom dates were noted each year. Data was collected on leaf yellowing, leaf drop, thinning, and leaf spot in July, August and September of each year. In addition, two replicates were also planted in Blairsville, Ga., in spring 2011, to assess performance in this colder environment (cold hardiness zone 6b). In March of 2011, rooted liners were shipped to a location in Bonsall, Calif. for evaluation.

*Vitex agnus-castus* is a deciduous shrub or small tree used in landscapes. This drought tolerant plant may be grown in cold hardiness zones 6 through 9. During cold winters in zone 6, it may die back to the ground, but will likely re-grow from the roots and produce a flowering shrub during the following summer, as flower buds are formed on new growth. Late spring freezes in zone 7 may also cause cold damage and dieback, but the plants recover and bloom during the summer. The new plant is expected to be distributed for landscape use in the U.S. and perhaps in other countries.

SUMMARY OF THE INVENTION

'V0509A-7' has been grown in an irrigated field plot in Griffin, Ga. and in a non-irrigated plot in Blairsville, Ga. Plants have been fertilized annually in the spring. Height and width were measured annually.

The following characteristics have been consistently observed in the original plant of this new variety and in asexually propagated progeny grown from stem cuttings and, to the best knowledge of the inventors, their combination forms the unique characteristics of 'V0509A-7' as a new and distinct cultivar. Asexual propagation by cuttings has proven that these characteristics are firmly fixed in succeeding asexually propagated generations.

1. Upright, larger panicles.
2. White flowers borne more closely together along the rachis.
3. More stunning floral display.

Comparison: 'V0509A-7' is an improved white *Vitex*, as compared to the industry standard, 'Silver Spires', the only commonly available white *Vitex*. 'Silver Spires' is a smaller plant than 'V0509A-7' (Table 1). 'V0509A-7' plants began blooming in the spring one week earlier than 'Silver Spires' two out of three years evaluated (Table 2). Both have minimal to moderate repeat blooming during summer and fall, though variation was observed in different years (Table 3). Panicles on 'V0509A-7' are longer and have a greater diameter than those on 'Silver Spires' (Table 4, FIG. 1). Furthermore, the distance between the pedicles on the rachis of the panicles of 'V0509A-7' was 1.3 cm versus 2.1 cm on 'Silver Spires' (Table 4, FIG. 1), placing the flowers closer together. These morphological differences result in a much showier floral display on 'V0509A-7' (FIG. 2). Flower petals on both 'V0509A-7' and 'Silver Spires' are white, though the anthers and filaments on 'V0509A-7' are purple. Panicles are generally held upright on 'V0509A-7', in contrast to 'Silver Spires' where panicles are oriented more randomly (FIG. 2). In comparison to the white flowers of the new variety 'Abbeville Blue' has flowers that are blue in coloration. The new variety 'V0509A-7' has white N155B flowers; while 'Abbeville Blue' has violet N88B flowers.

Selection 'V0509A-7' and 'Silver Spires' had no cold damage in any of the four years evaluated in Griffin, Ga. In Blairsville, Ga., a spring freeze in April 2012 caused extensive damage to all of the *Vitex* in our test plot. Both 'Silver Spires' and 'V0509A-7' lost all of the newly emerged foliage. Both recovered, though 'Silver Spires' had several dead branches, and flowering was delayed until August. Selection 'V0509A-7' recovered more quickly, had very few dead branches, and flowered in July.

TABLE 1

Height and width (cm) of *Vitex* 'V0509A-7' and 'Silver Spires' one, two and three years after planting in a field plot in Griffin, Georgia. Data for 'V0509A-7' is the average of three plants and 'Silver Spires' is based on one plant.

| Entry | Year 1 | Year 2 | Year 3 |
|---|---|---|---|
| 'V0509A-7' | 178 H × 242 W | 228 H × 285 W | 333 H × 338 W |
| 'Silva Spires' | 145 H × 196 W | 233 H × 272 W | 273 H × 318 W |

TABLE 2

First bloom dates of V0509A-7 and 'Silver Spires' grown in Griffin, GA.

| Entry | First bloom 2011 | First bloom 2012 | First bloom 2013 |
|---|---|---|---|
| 'V0509A-7' | 5-30 | 5-21 | 6-10 |
| 'Silver Spires' | 6-06 | 5-21 | 6-17 |

TABLE 3

Repeat flowering in July, August, September and October in 2011, 2012, and 2013.

| Entry | Year | July | August | September | October |
|---|---|---|---|---|---|
| 'V0509A-7' | 2011 | 0* | 0 | 0.3 | 0 |
| | 2012 | 0.3 | 1.5 | 2.2 | 2.3 |
| | 2013 | 1.0 | 0.2 | 2.8 | 2.7 |
| 'Silver Spires' | 2011 | 1.0 | 1.0 | 2.5 | 0 |
| | 2012 | 0 | 1.5 | 3.0 | 3.0 |
| | 2013 | 1.0 | 0 | 0.5 | 0.5 |

*Repeat flowering was rated using the following scale: 0 = no flowering; 1 = 10% full bloom; 2 = 20 to 30% full bloom; 3 = 40 to 50% full bloom; 4 = at least 60% full bloom.

TABLE 4

Panicle length, diameter and number of secondary peduncles per panicle, averaged over 2011; 2012, and 2013. Measurements were made on four typical or average- sized panicles per plant per year. The distance between the pedicels on the rachis was based on measurements on four typical panicles.

| Entry | Mean panicle length (cm) | Mean diameter (cm) of sub-panicles | Number of secondary peduncles/panicle | Distance between pedicels on the rachis* (cm) |
|---|---|---|---|---|
| 'V0509A-7' | 23 | 3.2 | Two to six | 1.3 |
| 'Silver Spires' | 21 | 1.9 | Two to five | 2.1 |

*Measurements were made between the second and third pedicels from the bottom of the central panicle.

BRIEF DESCRIPTION OF THE PHOTOGRAPHS

The accompanying colored photographic illustrations show the overall appearance and distinct characteristics of the new cultivar of *Vitex agnus-castus*. The colors in the photographs are as close as possible with the photographic and printing technology utilized.

DETAILED BOTANICAL DESCRIPTION

Figure 1:
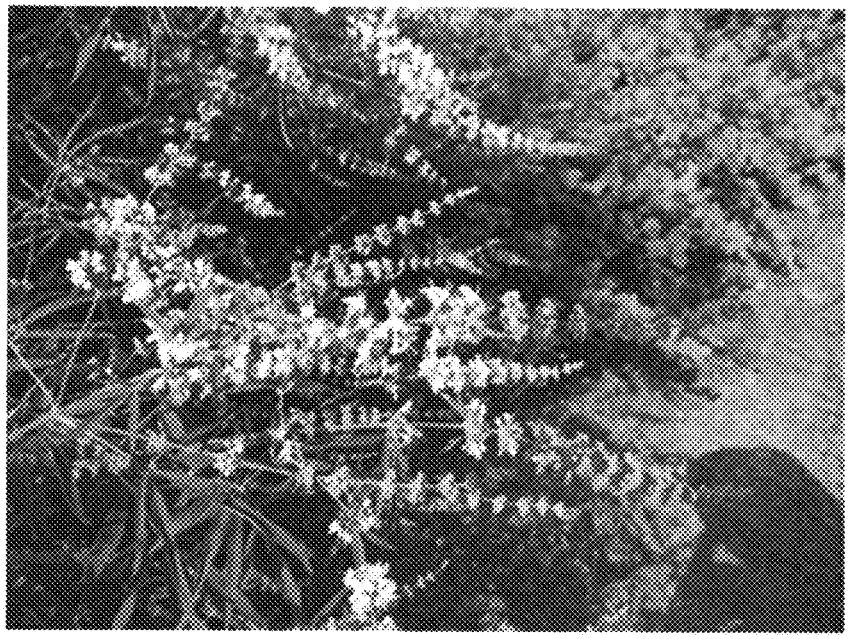
FIG. 1 is a photograph of flowers of 'Silver Spires' (top) and 'V0509A-7' (bottom). Photos were taken from flower clusters of similar blooming stage on Jun. 24, 2013.
Figure 1:
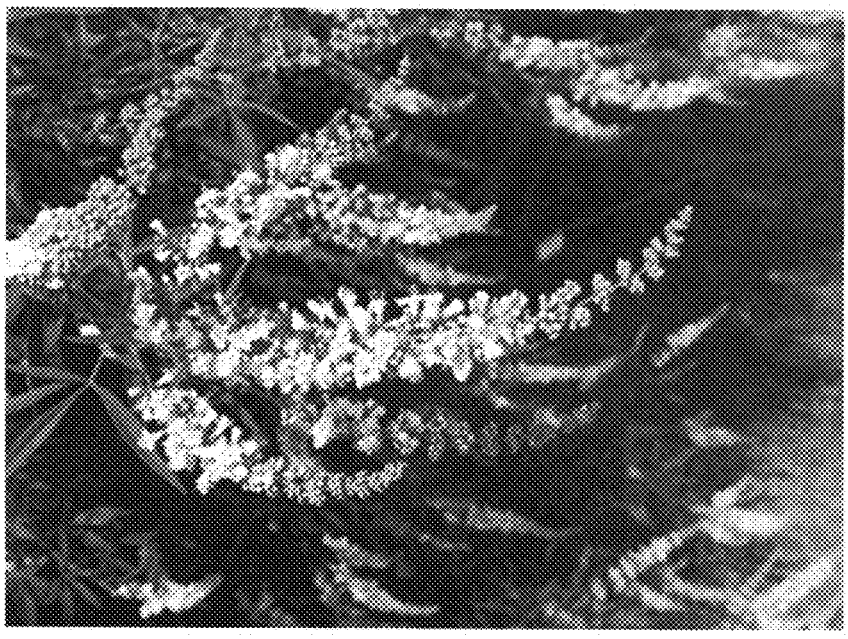
Figure 2:
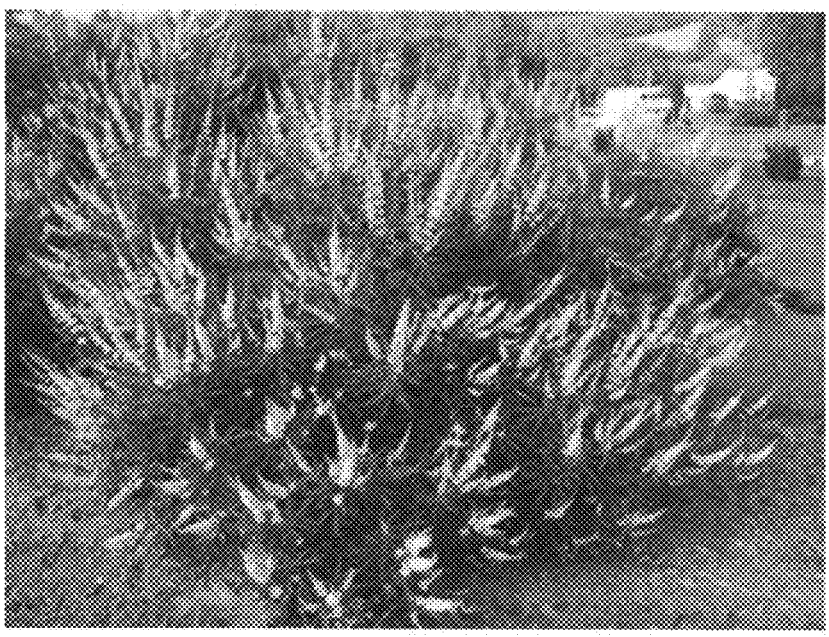
FIG. 2 is a photograph of 'V0509A-7' (top) and 'Silver Spires' (bottom). 'V0509A-7' has a more stunning display than 'Silver Spires', and the panicles on 'V0509A-7' are more upright. Photos were taken Jul. 12, 2013, on plants in Blairsville, Ga., that had been in the field for two years.
Figure 2:
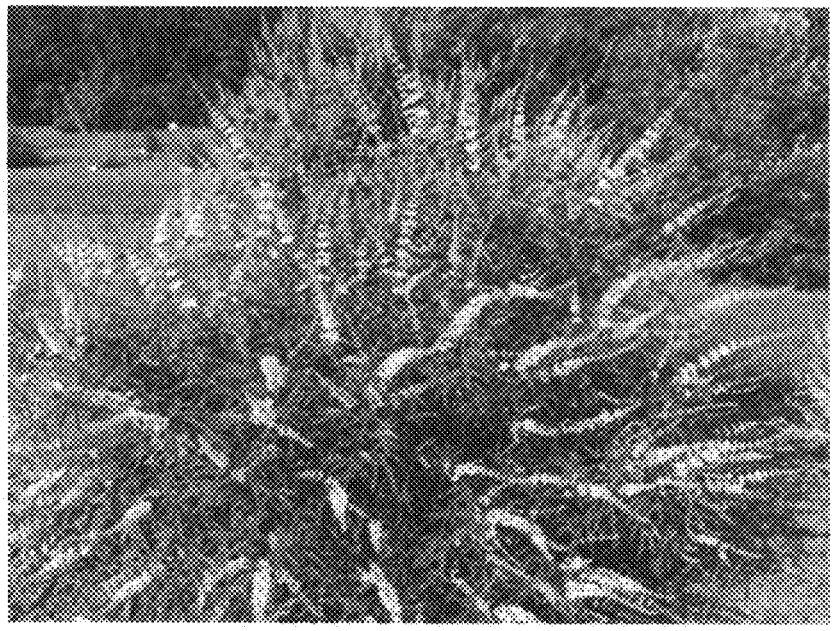

The following is a detailed description of the *Vitex agnus-castus* cultivar named 'V0509A-7'. Data was collected in Griffin, Ga. from three year old plants grown from cuttings and growing outdoors. 'V0509A-7' has not been tested under all possible conditions hence, phenotypic differences may be observed with variations in environmental conditions without any variance in genotype.

Parentage:

*Female parent*.—'Abbeville Blue'.

*Male parent*.—Either 'Abbeville Blue' or 'Silver Spires'. Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society (R.H.S.), London, England. This description is from observations of typical three year old plants growing in Griffin, Ga.

Habit: Open, spreading, upright.

Size (height×width): 373 cm×402 cm.

Texture: Medium coarse.

Stems:

*First year*.—Color — Grey-Brown N199A. Diameter — 5 mm. Pubescence — dense, minute curved hairs, scattered longer curved hairs. Exfoliation — None. Shape — round. Pith — Type: Solid. Diameter: 3 mm. Color: Yellow-Green 150D. Odor — strong, spicy, acrid. Lenticels — none observed. Internode length — 8.cm.

*Second year*.—Color — Grey-Green 197A. Diameter — 7-8 mm. Exfoliation — none.

Vegetative buds:

*Arrangement*.—Opposite.

*Type*.—Valvate.

*Size*.—1 mm×1 mm.

*Scale number*.—2.

*Scale color*.—Greyed-Orange 177D.

*Position/disposition*.—45°.

*Number at node*.—2, one on each side.

*Pubescence*.—Dense minute hairs, wooly.

*Shape*.—Domed, rounded.

Leaf scar:

*Shape*.—Cup shaped.

*Vascular bundle traces*.—3, horizontal and oval.

*Pubescence*.—Dense minute hairs around perimeter.

*Position of bud*.—Just above.

*Color differentiation*.—Yellow-Green 144A.

*Size*.—2.5×3 mm.

Trunk or large stems:

*Colors*.—Mix of Greyed-White 156A and Greyed-Brown 199D.

*Size stem that exfoliation begins on*.—Approximately 5 cm.

*Diameter*.—3 to 5 cm.

*Texture*.—Mostly smooth, striations start at approx. 3 cm, cracking by 5.0 cm.

Leaf:

*Color through seasons*.—Emerging — mid April. Upper: Yellow-Green 144A. Lower: Greyed-Green 191B. Summer — Mid July. Upper: Green 137A. Lower: Greyed-Green 191B. Fall — September. Upper: Yellow-Green 147A. Lower Greyed-Green 191B.

*Mature size*.—15 cm×19 cm.

*Apex*.—Acute.

*Base*.—Acute.

*Margin*.—Mostly entire.

*Shape*.—Palmate, mostly 7 leaflets. Lobes — none. Sinuses — None.

*Vein color*.—Greyed-Green 194D.

*Pubescence*.—Upper surface has many scattered hairs, with more along the veins, slightly glandular surface. Lower leaf is more densely hairy and has a very glandular surface.

*Arrangement on stem*.—Opposite.

*Venation*.—Pinnate.

*Texture*.—Thickness — 0.025 mm. Degree of waxiness of surfaces — slightly waxy but dull on upper surface, completely dull on lower surface.

*Foliage fragrance*.—Mild, spicy.

*Average size of the leaflets*.—The leaflets of five leaves that each had five leaflets per leaf were measured. The leaflets are arranged palmately, going from small to medium to large to medium to small. Mean lengths and widths of each of the five leaflets are as follows: 40.0 mm long, 9.4 mm wide; 63.4 mm long, 11.6 mm wide; 80.2 mm long, 16.6 mm wide; 60.4 mm long, 13.4 mm wide; 38.2 mm long, 10.4 mm wide.

Petiole:

*Length*.—6 cm.

*Shape*.—Round.

*Color*.—Upper Greyed-Orange 177A, lower Yellow-Green 145B.

*Pubescence*.—Densely covered in minute curved hairs.

*Diameter*.—1.6 mm.

Flower buds:

*Size*.—7 mm×4 mm.

*Color*.—Red-Purple 69D.

*Shape*.—Teardrop.

*Pubescence*.—Glandular surface, hairs laying flat.

*Time of full maturity*.—Early summer.

*Time range for showiness*.—Mid-June through September.

Flower:

*Inflorescence(s)*.—Type — elongated panicle, compound. Size — 23 cm long×8 cm wide (largest in panicle); individual floret 10 mm long×8 mm wide. Color — At emergence: White N155B. Full bloom: White N155B. Fading: White N155B. Peduncle — Color: Greyed-Green 193A. Pubescence: short hairs, glandular. Number of individual flowers per inflorescence — 271-550. Fragrance — Faint, slightly sweet.

Petal(s):

*Size*.—10 mm×8 mm.

*Shape*.—Zygomorphic, gamopetalous, bilabiate.

*Apex*.—5 lobes rounded and slightly curled.

*Base*.—Funnel.

*Margin*.—Slightly curled.

*Pubescence*.—Mostly glabrous, scattered glandular with thick tuft of hairs inside base and many flat, glandular hairs outside; a few longer hairs on anterior petal.

*Texture*.—Mostly smooth, slightly punctate.

*Color at peak of bloom*.—Upper surface — White N155B. Lower surface — White N155B.

*Pedicels*.—Color — Greyed-Green 193A. Pubescence — glandular, very dense short hairs. Length — 2-3 mm.

*Sepals*.—Size (l×w) — 3 mm×2 mm. Shape — united, slightly lobed. Apex — slightly lobed. Base — united, short tubular. Margin — smooth. Pubescence — glandular, tomentose-short hairs. Texture — hoary. Color at peak of bloom — Upper surface: Greyed-Green 198A and Greyed-Green 193C. Lower surfaces: Yellow-Green 144C with Violet-Blue 93C.

*Male reproductive structures*.—Number — 4. Anther — Size (l×w): 1.5 mm×0.5 mm. Color: Violet 86A. Filament — Size (l×w): 7 mm×0.5 mm. Color: Purple 76B. Pollen color — White 155C. Pubescence — thick tuft at base.

*Female reproductive structures*.—Pistil — Shape: tubular, bifid. Size (l×w) — 6.5 mm×0.5 mm. Position — superior. Color — Violet 84B. Pubescence — thickly tufted hairs at base. Stigma — Shape: round, bifid. Color: White 155C. Pubescence: none. Style — Length: 6 mm. Shape: tubular, forked at stigma (bifid). Color: Violet 84B. Pubescence: none, but tufted at base. Ovary — Shape: round. Number: 1. Pubescence: scattered short hairs, numerous glands present on surface.

Fruit:

*Type*.—Drupe-like.

*Size (l×w)*.—3.5 mm×2.5 mm.

*Colors during ripening*.—Early — Yellow-Green 151B. Mid — Greyed-Orange 166B. Late — Brown 200A.

*Shape*.—Globular.
*Number per infructescence*.—1.
*Pubescence*.—Few scattered hairs.
*Number of carpels*.—2.
*Persistence*.—Mid to late summer through fall into winter.

Seed:

*Shape*.—Globular.
*Size*.—3.5 mm×2.5 mm, oval.
*Color*.—Brown 200A when fully ripe.
*Number per locule per ovary per fruit*.—1.
*Germination capacity*.—≈30%.
*Pubescence*.—Scattered minute hairs.

Disease and pest resistance: Pests and diseases have not been observed to date.

Hardiness: The plant has been grown in USDA hardiness zone 8a; the plant has also been successfully grown in USDA hardiness zone 6b, though in this zone the plants die back in cold winters, but they regrow and bloom in the summer.

What is claimed is:

1. A new and distinct cultivar of the *Vitex agnus-castus* plant named 'V0509A-7' substantially as illustrated and described therein.

* * * * *

'Silver Spires'

'V0509A-7'

'V0509A-7'

'Silver Spires'